US012577186B2

(12) United States Patent
Mizugaki et al.

(10) Patent No.: US 12,577,186 B2
(45) Date of Patent: Mar. 17, 2026

(54) METHOD FOR PRODUCING ETHER

(71) Applicants: OSAKA UNIVERSITY, Suita (JP); DAICEL CORPORATION, Osaka (JP)

(72) Inventors: Tomoo Mizugaki, Suita (JP); Katsumasa Sakoda, Suita (JP); Yuuichirou Hirai, Tokyo (JP); Yasuteru Kajikawa, Tokyo (JP)

(73) Assignees: OSAKA UNIVERSITY, Osaka (JP); DAICEL CORPORATION, Osaka (JP)

( * ) Notice: Subject to any disclaimer, the term of this patent is extended or adjusted under 35 U.S.C. 154(b) by 615 days.

(21) Appl. No.: 17/926,403

(22) PCT Filed: May 13, 2021

(86) PCT No.: PCT/JP2021/018184

§ 371 (c)(1),
(2) Date: Nov. 18, 2022

(87) PCT Pub. No.: WO2021/235309

PCT Pub. Date: Nov. 25, 2021

(65) Prior Publication Data

US 2023/0183158 A1 Jun. 15, 2023

(30) Foreign Application Priority Data

May 20, 2020 (JP) ................................ 2020-088155

(51) Int. Cl.

| | |
|---|---|
| ***C07C 41/01*** | (2006.01) |
| ***B01J 21/06*** | (2006.01) |
| ***B01J 23/28*** | (2006.01) |
| ***B01J 23/42*** | (2006.01) |
| ***B01J 23/652*** | (2006.01) |
| ***C07C 29/149*** | (2006.01) |

(52) U.S. Cl.

CPC ............ *C07C 41/01* (2013.01); *B01J 21/066* (2013.01); *B01J 23/28* (2013.01); *B01J 23/42* (2013.01); *B01J 23/6525* (2013.01); *C07C 29/149* (2013.01)

(58) Field of Classification Search

CPC .............................. C07C 29/149; C07C 41/01

See application file for complete search history.

(56) References Cited

U.S. PATENT DOCUMENTS 4,973,717 A 11/1990 Williams
2004/0122242 A1 * 6/2004 Campos .............. C07D 307/08 549/429

FOREIGN PATENT DOCUMENTS

JP 9-25253 A 1/1997

OTHER PUBLICATIONS

Zafeiratos, S. et al. "The effect of Mo oxides and TiO2 support on the chemisorption features of linearly adsorbed CO on Pt crystallites: an infrared and photoelectron spectroscopy study" Journal of Catalysis 232 (2005) 127-136 (Year: 2005).*

Chinese Office Action and Search Report for Chinese Application No. 202180035680.9, dated Oct. 11, 2023.

International Preliminary Report on Patentability and Written Opinion issued Nov. 17, 2022, in PCT/JP2021/018184.

International Search Report issued Jul. 20, 2021, in PCT/JP2021/018184.

Li et al., "Lewis Acid Promoted Ruthenium (II)-Catalyzed Etherifications by Selective Hydrogenation of Carboxylic Acids/Esters," Angew. Chem. Int. Ed. (2015), vol. 54, pp. 5196-5200.

* cited by examiner

*Primary Examiner* — Medhanit W Bahta

(74) *Attorney, Agent, or Firm* — Birch, Stewart, Kolasch & Birch, LLP

(57) ABSTRACT

Provided is a method for producing, from a carboxylic acid ester, a corresponding ether. In the method, the reaction product and catalyst can be easily separated, and a large amount of salt waste or hazardous waste is not discharged. The method for producing an ether includes reducing a carboxylic acid ester with molecular hydrogen in the presence of the following Catalyst and producing the corresponding ether, in which the —C(═O)O— group of the carboxylic acid ester has been converted to a —$CH_2O$— group: Catalyst: a catalyst in which the following $M^1$ and $M^2$ are supported as metal species on the following Support. $M^1$: platinum, ruthenium, rhodium, palladium, or iridium. $M^2$: molybdenum, rhenium, tungsten, or vanadium. Support: zirconium oxide, titanium oxide, cerium oxide, or hydroxyapatite.

6 Claims, No Drawings

METHOD FOR PRODUCING ETHER

TECHNICAL FIELD

The present disclosure relates to a method for producing, by reducing a carboxylic acid ester, a corresponding ether; the present disclosure also relates to an ester reduction catalyst. The present application claims priority from the Japanese Patent Application No. 2020-088155, filed in Japan on May 20, 2020, the content of which is incorporated herein by reference.

BACKGROUND ART

Long-chain alkyl ethers derived from fatty acids have a relatively low melting point and viscosity, making those compounds useful in fragrances, lubricants, surfactants, and cosmetics. Asymmetrical alkyl ethers are prepared primarily by the Williamson ether synthesis and the Ullmann ether reaction. However, these methods require the use of organic halides and strong bases, and have issues such as resulting in salt waste.

Direct reduction of esters allows for easy synthesis of asymmetrical ethers, and thus the approach is drawing attention. However, many of the known ester-to-ether reduction reactions use $LiAlH_4$ or silanes as the reducing agents, leading to the generation of hazardous waste. As such, it is desirable to establish an ester-to-ether reaction pathway that uses inexpensive molecular hydrogen as a reducing agent and that generates clean water only as a by-product.

In 2015, Beller et al. completed an ester-to-ether reduction reaction using molecular hydrogen as a reducing agent, the first successful reaction of this kind in the world (Non-Patent Document 1). Ethers were synthesized using ruthenium/triphos and $Al(OTf)_3$ as catalysts at a reaction temperature of from 130 to 160° C. and a hydrogen pressure of from 4 to 6 MPa. However, those catalysts were complex catalysts, which are difficult to be separated and recovered.

CITATION LIST

Non-Patent Literature

Non-Patent Document 1: Angew. Chem. Int. Ed. 2015, 54, 5196-5200

SUMMARY OF INVENTION

Technical Problem

As such, an object of the present disclosure is to provide a method capable of producing, from a carboxylic acid ester, a corresponding ether, the method allowing for easy separation of reaction products and catalyst and not involving the discharge of a large amount of salt waste or hazardous waste.

Another object of the present disclosure is to provide a heterogeneous catalyst capable of reducing a carboxylic acid ester with molecular hydrogen to produce the corresponding ether.

Solution to Problem

As a result of diligent research to solve the issues described above, the present inventors discovered that, use of a specific catalyst can produce, from a carboxylic acid ester and molecular hydrogen, a corresponding ether in a way that the reaction products and the catalyst are easily separable, and a large amount of salt waste or hazardous waste is not discharged, and hence completed the present disclosure.

That is, the present disclosure provides a method for producing an ether, the method including reducing a carboxylic acid ester with molecular hydrogen in the presence of the following Catalyst and producing a corresponding ether in which the —C(═O)O— group of the carboxylic acid ester has been converted to a —$CH_2$O— group.

Catalyst: a catalyst in which the following $M^1$ and $M^2$ are supported as metal species on the following Support:

$M^1$: platinum, ruthenium, rhodium, palladium, or iridium $M^2$: molybdenum, rhenium, tungsten, or vanadium Support: zirconium oxide, titanium oxide, cerium oxide, or hydroxyapatite The carboxylic acid ester is, for example, a compound represented by the following Formula (1):

[Chem. 1]

(1)

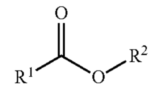

where in Formula (1), $R^1$ is a hydrogen atom, or an organic group having a carbon atom at an adjacent site to the carbonyl group in the Formula, and $R^2$ is an organic group having a carbon atom at a binding site with an oxygen atom in the Formula.

The catalyst may contain $M^2$ as a metal species in a range of from 0.05 to 1 mol per 1 mol of $M^1$ that is a metal species.

The present disclosure also provides an ester reduction catalyst in which the following $M^1$ and $M^2$ are supported as metal species on the following Support, the catalyst for use in reducing a carboxylic acid ester to give a corresponding ether, in which the —C(═O)O— group of the carboxylic acid ester has been converted to a —$CH_2$O— group:

$M^1$: platinum, ruthenium, rhodium, palladium, or iridium $M^2$: molybdenum, rhenium, tungsten, or vanadium Support: zirconium oxide, titanium oxide, cerium oxide, or hydroxyapatite.

Advantageous Effects of Invention

According to an embodiment of the present disclosure, the corresponding ether obtained by reducing a carboxylic acid ester with molecular hydrogen can be produced without a large amount of salt waste or hazardous waste being discharged. Furthermore, the separation of reaction products and catalyst is easy since the catalyst is a heterogeneous catalyst. The present disclosure allows for not only a reaction in a solvent but also a reaction without a solvent. The present disclosure enables the synthesis of not only symmetrical ethers but also asymmetrical ethers, giving the product a wide range of applications.

DESCRIPTION OF EMBODIMENTS

Catalyst

In an embodiment of the present disclosure, at least one catalyst, in which the following $M^1$ and $M^2$ are supported as metal species on the following Support, is used.

$M^1$: platinum, ruthenium, rhodium, palladium, or iridium $M^2$: molybdenum, rhenium, tungsten, or vanadium Support: zirconium oxide, titanium oxide, cerium oxide, or hydroxyapatite $M^1$ and $M^2$ to be supported on the support may be a simple metal, or a metal compound such as a metal salt, a metal oxide, a metal hydroxide, or a metal complex. From the perspective of catalytic activity, $M^1$ is preferably a simple metal, and $M^2$ is preferably a metal oxide. The metal species $M^1$ is particularly preferably platinum, and the metal species $M^2$ is particularly preferably molybdenum. Each of the metal species $M^1$ and $M^2$ may be one type of metal, or may be a combination of two or more types of metals.

The amount of $M^1$ supported (in terms of metal) is, for example, from 0.01 to 10 mmol/g, preferably from 0.05 to 5 mmol/g, and particularly preferably from 0.1 to 1 mmol/g, with respect to the support. By setting the dose of $M^1$ to the range described above, excellent catalytic activity and reaction selectivity can be obtained.

The amount of $M^2$ supported (in terms of metal) is, for example, from 0.001 to 1 mmol/g, preferably from 0.01 to 0.5 mmol/g, and particularly preferably from 0.01 to 0.1 mmol/g, with respect to the support. By setting the dose of $M^2$ to the range described above, excellent catalytic activity and reaction selectivity can be obtained.

The catalyst in an embodiment of the present disclosure is considered to have an active site at the interface of $M^1$ and $M^2$. From the perspective of catalytic activity, the amount of $M^2$ supported (in terms of metal) with respect to 1 mol of $M^1$ (in terms of metal) is, for example, from 0.05 to 1 mol, preferably from 0.1 to 0.5 mol, and more preferably from 0.15 to 0.35 mol.

In an embodiment of the present disclosure, the catalyst may contain a third metal species, other than $M^1$ and $M^2$, supported on the support. The amount of the third metal species supported (in terms of metal) is, for example, 200 mol % or less, preferably 150 mol % or less, more preferably 100 mol % or less, even more preferably 50 mol % or less, particularly preferably 10 mol % or less, most preferably 5 mol % or less, and especially preferably 1 mol % or less, with respect to the total amount of $M^1$ and $M^2$ supported (in terms of metal). When the amount of the third metal species supported exceeds the range described above, the effect of the present invention may not be readily achieved, which may be a result of shrunken active site.

In an embodiment of the present disclosure, $M^1$ and $M^2$ are used while being supported on a support. Having $M^1$ and $M^2$ supported on a support can increase the interface area of $M^1$ and $M^2$, and thereby increasing exposure of the active site.

In an embodiment of the present disclosure, zirconium oxide, titanium oxide, cerium oxide, or hydroxyapatite (HAP) is used as the catalyst support. By using zirconium oxide, titanium oxide, cerium oxide, or hydroxyapatite as the catalyst support, good catalytic activity, good reaction selectivity, and excellent durability can be achieved. The catalyst support is particularly preferably zirconium oxide.

The specific surface area of the support (zirconium oxide, titanium oxide, cerium oxide, or hydroxyapatite) is, for example, from 5 to 250 $m^2/g$, preferably from 10 to 100 $m^2/g$, from the perspective of catalytic activity.

For the hydroxyapatite, commercially available products such as the product with the trade name "Tricalcium Phosphate" (available from FUJIFILM Wako Pure Chemical Corporation) can be used.

The catalyst according to an embodiment of the present disclosure can be suitably used as an ester reduction catalyst for reducing a carboxylic acid ester to give a corresponding ether in which the $-C(=O)O-$ group of the carboxylic acid ester has been converted to a $-CH_2O-$ group.

In an embodiment of the present disclosure, since a catalyst including a support on which $M^1$ and $M^2$ are supported is used, the catalyst can be easily separated from the reaction products by physical separation methods, such as filtration or centrifugation, after completion of the reaction. The catalyst separated from the reaction products and recovered can be reused as is, or after, for example, being washed or dried. Furthermore, since zirconium oxide or hydroxyapatite is used as the support, the durability of the catalyst is excellent, and the dissolution of the catalyst into the reaction solution is suppressed; as such, good catalytic activity can be maintained even after repeated reuse or continuous long-term operation.

In an embodiment of the present disclosure, the catalyst can be used repeatedly (or the catalyst can be used for a long period of time in the case of continuous reaction) despite that relatively expensive metal species are used, as described above; accordingly, the production cost of ether can be reduced.

Method for Preparing Catalyst

The catalyst according to an embodiment of the present disclosure can be prepared, for example, by an impregnation method.

An impregnation method is a method for supporting a metal species on a support, the method including immersing a support in a solution (for example, an aqueous solution) prepared by dissolving a compound containing the metal species mentioned above (i.e., a metal compound) in a solvent (e.g., water), impregnating the support with the metal compound, and then subjecting the resulting product to drying and calcination. The supported amount of the metal species can be controlled by adjusting, for example, the concentration of the metal compound in the solution, or the immersion time of the support.

The catalyst in an embodiment of the present disclosure can be prepared by: a sequential impregnation method, in which a support is sequentially impregnated with a solution containing the metal species $M^1$ (a solution prepared by dissolving a compound containing the metal species $M^1$ in a solvent; hereinafter, the solution may be referred to as "$M^1$-containing solution") and then a solution containing the metal species $M^2$ (a solution prepared by dissolving a compound containing the metal species $M^2$ in a solvent; hereinafter, the solution may be referred to as "$M^2$-containing solution"); or, a co-impregnation method in which a support is simultaneously impregnated with an $M^1$-containing solution and an $M^2$-containing solution. When preparing the catalyst using the co-impregnation method, the catalyst may be prepared by impregnating the support with a mixed solution of the $M^1$-containing solution and the $M^2$-containing solution and subjecting the resulting product to drying and calcination; meanwhile, when preparing the catalyst using the sequential impregnation method, the catalyst may be prepared by impregnating the support with one of the $M^1$-containing solution and the $M^2$-containing solution, subjecting the resulting product to drying, impregnating the resulting product with the other of the $M^1$-containing solution and the $M^2$-containing solution, subjecting the resulting product to drying, and then subjecting the dried product to calcination.

For example, a catalyst including a support on which Pt as $M^1$ and Mo as $M^2$ are supported by a co-impregnation method (for example, Pt—Mo/support) can be prepared by: preparing a solution by dissolving a Pt compound (such as $H_2PtCl_6$) and an Mo compound [such as $(NH_4)_6Mo_7O_{24}\cdot 4H_2O$] in water; immersing a support (zirconium oxide, titanium oxide, cerium oxide, or hydroxyapatite) in the solution; then, subjecting the resulting product to distillation of water, drying, and calcination.

For example, a catalyst including a support on which Pt as $M^1$ and Mo as $M^2$ are sequentially supported in the order of Mo—Pt (for example, Pt/Mo/support) can be prepared by: preparing a solution by dissolving a Mo compound [such as $(NH_4)_6Mo_7O_{24}\cdot 4H_2O$] in water; immersing a support (zirconium oxide, titanium oxide, cerium oxide, or hydroxyapatite) in the solution; subjecting the resulting product to distillation of water and drying; immersing the resulting product in a solution prepared by dissolving a Pt compound (such as $H_2PtCl_6$) in water; then, subjecting the resulting product to distillation of water, drying, and calcination.

The temperature at which the support is immersed in the solution is, for example, approximately from 10 to 80° C.

The time of immersing the support in the solution is, for example, from 1 to 30 hours, preferably from 1 to 5 hours.

The calcination is carried out by, for example, using a muffle furnace. The calcination temperature is, for example, from 300° C. to lower than 700° C. The calcination time is, for example, from 1 to 5 hours. When the calcination temperature exceeds the range described above, the catalytic activity tends to decrease sharply, which may be because the metal species supported on the support aggregate. The calcination temperature is preferably from 350 to 650° C., particularly preferably from 400 to 550° C., and especially preferably from 450 to 550° C., from the perspective of enhancing catalytic activity.

Reduction treatment may be further performed after calcination. Examples of reducing agents used for the reduction treatment include hydrogen ($H_2$).

The temperature and time of the reduction treatment are, for example, approximately from 0.5 to 5 hours (preferably from 0.5 to 2 hours) at a temperature of from 0 to 600° C. (preferably from 100 to 200° C.).

The catalyst prepared by the preparation method described above may then be subjected to, for example, a washing treatment (washing with water, an organic solvent, or the like), or a drying treatment (drying by vacuum drying, or the like).

Substrate

In an embodiment of the present disclosure, the method for producing an ether uses a carboxylic acid ester as a substrate. Examples of the carboxylic acid ester include an ester of a carboxylic acid and a hydroxyl group-containing compound, the carboxylic acid being selected from the group consisting of an aliphatic carboxylic acid, an alicyclic carboxylic acid, an aromatic carboxylic acid, and a heterocyclic carboxylic acid, while the hydroxyl group-containing compound being selected from the group consisting of an aliphatic alcohol, an alicyclic alcohol, an aromatic alcohol, a heterocyclic alcohol, and a phenol. The carboxylic acid ester may be a compound having one ester bond [—C(═O)O—] in one molecule, or may be a compound having two or more ester bonds in one molecule.

A representative example of the carboxylic acid ester includes a compound represented by the following Formula (1):

[Chem. 2]

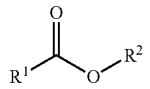

(1)

where in Formula (1), $R^1$ is a hydrogen atom, or an organic group having a carbon atom at an adjacent site to the carbonyl group in the Formula, and $R^2$ is an organic group having a carbon atom at a binding site with an oxygen atom in the Formula.

Examples of the "organic group having a carbon atom at an adjacent site to the carbonyl group in the Formula" for $R^1$ and the "organic group having a carbon atom at a binding site with an oxygen atom in the formula" for $R^2$ include a group in which two or more of an aliphatic hydrocarbon group, an alicyclic hydrocarbon group, an aromatic hydrocarbon group, and a heterocyclic group are bonded, via or not via one or more linking groups selected from the group consisting of an ether bond, a thioether bond, —NH—, —C(═O)—, and —C(═S)—.

Examples of the aliphatic hydrocarbon group include: straight-chain or branched alkyl groups having from 1 to 20 carbons (preferably from 1 to 12 carbons), such as a methyl group, an ethyl group, a propyl group, an isopropyl group, a butyl group, a pentyl group, an octyl group, a 2-ethylhexyl group, a decyl group, a dodecyl group, a tetradecyl group, a hexadecyl group, and a octadecyl group; and straight-chain or branched alkenyl groups having from 2 to 20 carbons (preferably 2 to 12 carbons), such as a vinyl group, an allyl group, a propenyl group, a 1-butenyl group, a 2-butenyl group, a 1-pentenyl group, and a 2-pentenyl group.

Examples of the alicyclic hydrocarbon group include: cycloalkyl groups having from 3 to 10 carbons (preferably from 3 to 6 carbons), such as a cyclopentyl group, a cyclohexyl group, and a cycloheptyl group; cycloalkenyl groups having from 3 to 10 carbons (preferably from 3 to 6 carbons), such as a cyclopropenyl group, a cyclobutenyl group, a cyclopentenyl group, a cyclohexenyl group, and a cyclooctenyl group.

Examples of the aromatic hydrocarbon group include aryl groups having from 6 to 20 carbons, such as a phenyl group, a biphenyl group, a naphthyl group, a binaphthyl group, and an anthracenyl group.

Examples of the heterocyclic group include aromatic or non-aromatic heterocyclic groups having one or more heteroatoms selected from the group consisting of an oxygen atom, a sulfur atom, and a nitrogen atom, such as a 2-furyl group, a 2-thienyl group, a 2-pyridyl group, a 3-pyridyl group, a 4-pyridyl group, a 2-quinolyl group, a 4-piperidinyl group, and a 2-morpholinyl group.

The aliphatic hydrocarbon group, the alicyclic hydrocarbon group, the aromatic hydrocarbon group, and the heterocyclic group may have a substituent. Examples of the substituent include a $C_{1-5}$ alkyl group, a $C_{1-5}$ alkoxy group, a $C_{6-10}$ aryl group, a $C_{6-10}$ aryloxy group, a $C_{7-11}$ aralkyl group, a $C_{7-11}$ aralkyloxy group, an oxo group, a halogen atom, and a $C_{1-5}$ haloalkyl group.

Method for Producing Ether

In the method for producing an ether according to an embodiment of the present disclosure, the carboxylic acid ester serving as a substrate is reduced by molecular hydrogen in the presence of the catalyst described above, and the —C(═O)O— group contained in the ester is converted to a —$CH_2$O— group, resulting in a corresponding ether.

The method for producing an ether according to an embodiment of the present disclosure produces an ether corresponding to the substrate (carboxylic acid ester) used. For example, the use of a carboxylic acid ester represented by Formula (1) above as the substrate results in an ether represented by the following Formula (2). By selecting different substrates, various symmetrical ethers or asymmetrical ethers can be produced.

[Chem. 3]

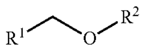
(2)

where in Formula (2), $R^1$ and $R^2$ are the same as those described above.

There are two types of reaction mechanisms from a carboxylic acid ester to an ether, one being a process of direct deoxidation, the other being a process of hydrolyzation of a carboxylic acid ester to produce a carboxylic acid and an alcohol (alcohol-1), reduction of the carboxylic acid to produce an alcohol (alcohol-2), and dehydration reaction of the alcohol-2 and the alcohol-1 to produce an ether. Since a corresponding ether is not produced even when a carboxylic acid and an alcohol are used as raw materials, it is considered that the present reaction proceeds by the mechanism in which direct deoxidation occurs from an ester.

The amount of the catalyst used (in terms of the metal platinum, ruthenium, rhodium, palladium, or iridium contained in the catalyst) is, for example, from 0.01 to 30 mol %, preferably from 0.1 to 10 mol %, particularly preferably from 0.5 to 5 mol %, most preferably from 1 to 5 mol %, of the substrate.

Furthermore, the amount of the catalyst used (in terms of the metal molybdenum, rhenium, tungsten, or vanadium contained in the catalyst) is, for example, from 0.01 to 10 mol %, preferably from 0.05 to 5 mol %, and particularly preferably from 0.1 to 2 mol %, of the substrate.

When the catalyst is used in the range described above, the substrate can be efficiently reduced to produce the corresponding ether in good yield.

The reduction reaction using hydrogen is carried out, for example, by a method of carrying out the reaction in a hydrogen atmosphere, or a method of bubbling hydrogen gas.

In an embodiment of the present disclosure, the reduction of the —C(═O)O— group to the —$CH_2$O— group can proceed rapidly because of the use of the catalyst described above. The hydrogen pressure during the reduction reaction is, for example, from 0.1 to 20 MPa, preferably from 1 to 15 MPa, more preferably from 2 to 10 MPa, and particularly preferably from 2.5 to 8 MPa.

The reaction temperature of the reduction reaction is, for example, from 20 to 250° C., preferably from 50 to 230° C., more preferably from 70 to 220° C. (such as from 80 to 180° C.), and particularly preferably from 120 to 200° C. (such as from 90 to 160° C.). By setting the reaction temperature to be within the range described above, the reduction reaction of the substrate is promoted, decomposition of the target object can be suppressed, and an ether can be obtained in good yield.

The reaction time of the reduction reaction is, for example, from 0.5 to 200 hours, preferably from 0.6 to 36 hours, more preferably from 1 to 15 hours, and particularly preferably from 2 to 10 hours. By setting the reaction time to be within the range described above, the reduction reaction of the substrate is promoted, decomposition of the target object can be suppressed, and an ether can be obtained in good yield.

The reduction reaction can be performed by any method, such as a batch method, a semi-batch method, and a continuous method.

The reduction reaction is preferably carried out in the liquid phase. In other words, the reduction reaction according to an embodiment of the present invention is preferably a liquid-phase reaction.

The reduction reaction can be carried out with or without a solvent. Examples of the solvent include: ether-based solvents (chain ether or cyclic ether), such as diethyl ether, diisopropyl ether, dibutyl ether, and 1,4-dioxane; hydrocarbon solvents (aliphatic hydrocarbons, alicyclic hydrocarbons, or aromatic hydrocarbons), such as hexane, octane, decane, dodecane, cyclohexane, and toluene; halogenated hydrocarbon solvents, such as 1,2-dichloroethane and dichloromethane; alcohols, such as ethanol and isopropyl alcohol; and water. One of these can be used alone or two or more in combination. Note that when water is used as the solvent, a by-product alcohol tends to increase.

The amount of solvent to be used can be appropriately selected depending on, for example, the type of substrate. The concentration of the substrate in the total liquid to be subjected to the reaction (in the case of a batch method, the initial concentration of the substrate) is, for example, from 0.01 to 100 wt. %, preferably from 0.1 to 50 wt. %, and more preferably from 1 to 20 wt. %.

In the method for producing an ether according to an embodiment of the present disclosure, a heterogeneous catalyst is used; as such, the products and the catalyst can be easily separated and recovered by filtration or the like after the completion of the reaction. Therefore, the catalyst can be easily reused. Further, the method for producing an ether according to an embodiment of the present disclosure generates clean water as the main by-product, and does not result in the discharge of large amounts of salt waste or hazardous waste.

After the completion of the reaction, the resulting reaction products can be separated and purified by: a separation method, such as filtration, concentration, distillation, extraction, crystallization, recrystallization, and column chromatography; or a separation method in combination thereof.

The method for producing an ether according to an embodiment of the present disclosure allows the conversion of a carboxylic acid ester serving as a substrate to a corresponding ether.

Each aspect disclosed in the present specification can be combined with any other feature disclosed herein. Note that each of the configurations, combinations thereof, and the like in each of the embodiments are an example, and various additions, omissions, and other changes may be made as appropriate without departing from the spirit of the present disclosure. The present disclosure is not limited by the embodiments and is limited only by the claims.

EXAMPLES

Hereinafter, the present disclosure will be described in detail with reference to examples.

Preparation Example 1

Preparation of Catalyst: Sequential Impregnation Method 0.0088 g of $(NH_4)_6Mo_7O_{24}\cdot 4H_2O$ was dissolved in 50 mL of water to prepare a Mo solution. 1.0 g of zirconium oxide ($ZrO_2$, specific surface area: 22.1 $m^2/g$, reference catalyst "JRC-ZRO-8" by the Catalysis Society of Japan) was immersed in the Mo solution for 4 hours at room temperature (25° C.). After immersion, water was distilled off using a rotary evaporator, and drying was performed at 110° C.

After drying, in a Pt solution prepared by dissolving 0.0820 g of $H_2PtCl_6$ in 50 mL of water, the zirconium oxide was immersed at room temperature (25° C.) for 4 hours. After immersion, water was distilled off using a rotary evaporator, and drying was performed at 110° C. Then, the dried product was subjected to calcination in an air atmosphere in a muffle furnace at 500° C. for 3 hours, resulting in a catalyst (1) [$Pt/Mo/ZrO_2$, amount of Pt supported: 0.2 mmol/g (support), amount of Mo supported: 0.05 mmol/g (support), Mo/Pt (molar ratio)=0.25].

Preparation Example 2

Preparation of Catalyst: Co-impregnation Method 0.0820 g of $H_2PtCl_6$ and 0.0088 g of $(NH_4)_6Mo_7O_{24}\cdot 4H_2O$ were dissolved in 50 mL of water to prepare a solution. 1.008 g of zirconium oxide ($ZrO_2$, specific surface area: 22.1 $m^2/g$, reference catalyst "JRC-ZRO-8" by the Catalysis Society of Japan) was immersed in the solution for 4 hours at room temperature (25° C.). After immersion, water was distilled off in a rotary evaporator under reduced pressure. This resulted in a powder. Then, the resulting power was subjected to calcination in an air atmosphere in a muffle furnace at 500° C. for 3 hours, resulting in a catalyst (2) [$Pt—Mo/ZrO_2$, amount of Pt supported: 0.2 mmol/g (support), amount of Mo supported: 0.05 mmol/g (support), Mo/Pt (molar ratio)=0.25].

Preparation Example 3

Preparation of Catalyst: Sequential Impregnation Method 0.0820 g of $H_2PtCl_6$ was dissolved in 50 mL of water to prepare a Pt solution. 1.0 g of zirconium oxide ($ZrO_2$, specific surface area: 22.1 $m^2/g$, reference catalyst "JRC-ZRO-8" by the Catalysis Society of Japan) was immersed in the Pt solution for 4 hours at room temperature (25° C.). After immersion, water was distilled off in a rotary evaporator under reduced pressure, and drying was performed at 110° C.

After drying, in a solution prepared by dissolving 0.0088 g of $(NH_4)_6Mo_7O_{24}\cdot 4H_2O$ in 50 mL of water, the zirconium oxide was immersed at room temperature (25° C.) for 4 hours. After immersion, water was distilled off using a rotary evaporator under reduced pressure, and drying was performed at 110° C. Then, the dried product was subjected to calcination in an air atmosphere in a muffle furnace at 500° C. for 3 hours, resulting in a catalyst (3) [$Mo/Pt/ZrO_2$, amount of Pt supported: 0.2 mmol/g (support), amount of Mo supported: 0.05 mmol/g (support), Mo/Pt (molar ratio)=0.25].

Preparation Example 4

Preparation of Catalyst: Impregnation Method 0.0088 g of $(NH_4)_6Mo_7O_{24}\cdot 4H_2O$ was dissolved in 50 mL of water to prepare a Mo solution. 1.001 g of zirconium oxide ($ZrO_2$, specific surface area: 22.1 $m^2/g$, reference catalyst "JRC-ZRO-8" by the Catalysis Society of Japan) was immersed in the Mo solution for 4 hours at room temperature (25° C.). After immersion, water was distilled off in a rotary evaporator under reduced pressure, and drying was performed at 110° C. Then, the dried product was subjected to calcination in an air atmosphere in a muffle furnace at 500° C. for 3 hours, resulting in a catalyst (4) [$Mo/ZrO_2$, amount of Mo supported: 0.05 mmol/g (support)].

Preparation Example 5

Preparation of Catalyst: Sequential Impregnation Method 0.0134 g of $(NH_4)ReO_4$ was dissolved in 50 mL of water to prepare a Re solution. 1.0 g of zirconium oxide ($ZrO_2$, specific surface area: 22.1 $m^2/g$, reference catalyst "JRC-ZRO-8" by the Catalysis Society of Japan) was immersed in the Re solution for 4 hours at room temperature (25° C.). After immersion, water was distilled off in a rotary evaporator under reduced pressure, and drying was performed at 110° C.

After drying, in a Pt solution prepared by dissolving 0.0820 g of $H_2PtCl_6$ in 50 mL of water, the zirconium oxide was immersed at room temperature (25° C.) for 4 hours. After immersion, water was distilled off using a rotary evaporator under reduced pressure, and drying was performed at 110° C. Then, the dried product was subjected to calcination in an air atmosphere in a muffle furnace at 500° C. for 3 hours, resulting in a catalyst (5) [$Pt/Re/ZrO_2$, amount of Pt supported 0.2 mmol/g (support), amount of Re supported: 0.05 mmol/g (support), Re/Pt (molar ratio)=0.25].

Preparation Example 6

Preparation of Catalyst: Sequential Impregnation Method 0.0128 g of $(NH_4)_{10}H_2(W_2O_7)_6$ was dissolved in 50 mL of water to prepare a W solution. 1.0 g of zirconium oxide ($ZrO_2$, specific surface area: 22.1 $m^2/g$, reference catalyst "JRC-ZRO-8" by the Catalysis Society of Japan) was immersed in the W solution for 4 hours at room temperature (25° C.). After immersion, water was distilled off in a rotary evaporator under reduced pressure, and drying was performed at 110° C.

After drying, in a Pt solution prepared by dissolving 0.0820 g of $H_2PtCl_6$ in 50 mL of water, the zirconium oxide was immersed at room temperature (25° C.) for 4 hours. After immersion, water was distilled off using a rotary evaporator under reduced pressure, and drying was performed at 110° C. Then, the dried product was subjected to calcination in an air atmosphere in a muffle furnace at 500° C. for 3 hours, resulting in a catalyst (6) [$Pt/W/ZrO_2$, amount of Pt supported: 0.2 mmol/g (support), amount of W supported: 0.05 mmol/g (support), W/Pt (molar ratio)=0.25].

Preparation Example 7

Preparation of Catalyst: Sequential Impregnation Method 0.0058 g of $NH_4VO_3$ was dissolved in 50 mL of water to prepare a V solution. 1.0 g of zirconium oxide ($ZrO_2$, specific surface area: 22.1 $m^2/g$, reference catalyst "JRC-ZRO-8" by the Catalysis Society of Japan) was immersed in the V solution for 4 hours at room temperature (25° C.). After immersion, water was distilled off in a rotary evaporator under reduced pressure, and drying was performed at 110° C.

After drying, in a Pt solution prepared by dissolving 0.0820 g of $H_2PtCl_6$ in 50 mL of water, the zirconium oxide was immersed at room temperature (25° C.) for 4 hours. After immersion, water was distilled off using a rotary evaporator under reduced pressure, and drying was performed at 110° C. Then, the dried product was subjected to calcination in an air atmosphere in a muffle furnace at 500° C. for 3 hours, resulting in a catalyst (7) [Pt/V/$ZrO_2$, amount of Pt supported: 0.2 mmol/g (support), amount of V supported: 0.05 mmol/g (support), V/Pt (molar ratio)=0.25].

Preparation Example 8

Preparation of Catalyst: Sequential Impregnation Method 0.0134 g of $(NH_4)ReO_4$ was dissolved in 50 mL of water to prepare a Re solution. 1.0 g of zirconium oxide ($ZrO_2$, specific surface area: 22.1 $m^2$/g, reference catalyst "JRC-ZRO-8" by the Catalysis Society of Japan) was immersed in the Re solution for 4 hours at room temperature (25° C.). After immersion, water was distilled off in a rotary evaporator under reduced pressure, and drying was performed at 110° C.

After drying, in a Ru solution prepared by dissolving 0.0415 g of $RuCl_3$ in 50 mL of water, the zirconium oxide was immersed at room temperature (25° C.) for 4 hours. After immersion, water was distilled off using a rotary evaporator under reduced pressure, and drying was performed at 110° C. Then, the dried product was subjected to calcination in an air atmosphere in a muffle furnace at 500° C. for 3 hours, resulting in a catalyst (8) [Ru/Re/$ZrO_2$, amount of Ru supported: 0.2 mmol/g (support), amount of Re supported: 0.05 mmol/g (support), Re/Ru (molar ratio)=0.25].

Preparation Example 9

Preparation of Catalyst: Sequential Impregnation Method 0.0128 g of $(NH_4)_{10}H_2(W_2O_7)_6$ was dissolved in 50 mL of water to prepare a W solution. 1.0 g of zirconium oxide ($ZrO_2$, specific surface area: 22.1 $m^2$/g, reference catalyst "JRC-ZRO-8" by the Catalysis Society of Japan) was immersed in the W solution for 4 hours at room temperature (25° C.). After immersion, water was distilled off in a rotary evaporator under reduced pressure, and drying was performed at 110° C.

After drying, in a Ru solution prepared by dissolving 0.0415 g of $RuCl_3$ in 50 mL of water, the zirconium oxide was immersed at room temperature (25° C.) for 4 hours. After immersion, water was distilled off using a rotary evaporator under reduced pressure, and drying was performed at 110° C. Then, the dried product was subjected to calcination in an air atmosphere in a muffle furnace at 500° C. for 3 hours, resulting in a catalyst (9) [Ru/W/$ZrO_2$, amount of Ru supported: 0.2 mmol/g (support), amount of W supported: 0.05 mmol/g (support), W/Ru (molar ratio)=0.25].

Preparation Example 10

Preparation of Catalyst: Sequential Impregnation Method 0.0058 g of $NH_4VO_3$ was dissolved in 50 mL of water to prepare a V solution. 1.0 g of zirconium oxide ($ZrO_2$, specific surface area: 22.1 $m^2$/g, reference catalyst "JRC-ZRO-8" by the Catalysis Society of Japan) was immersed in the V solution for 4 hours at room temperature (25° C.). Water was distilled off in a rotary evaporator under reduced pressure, and drying was performed at 110° C.

After drying, in a Ru solution prepared by dissolving 0.0415 g of $RuCl_3$ in 50 mL of water, the zirconium oxide was immersed at room temperature (25° C.) for 4 hours. After immersion, water was distilled off using a rotary evaporator under reduced pressure, and drying was performed at 110° C. Then, the dried product was subjected to calcination in an air atmosphere in a muffle furnace at 500° C. for 3 hours, resulting in a catalyst (9) [Ru/V/$ZrO_2$, amount of Ru supported: 0.2 mmol/g (support), amount of V supported: 0.05 mmol/g (support), V/Ru (molar ratio)=0.25].

Preparation Example 11

Preparation of Catalyst: Sequential Impregnation Method 0.0134 g of $(NH_4)ReO_4$ was dissolved in 50 mL of water to prepare a Re solution. 1.0 g of zirconium oxide ($ZrO_2$, specific surface area: 22.1 $m^2$/g, reference catalyst "JRC-ZRO-8" by the Catalysis Society of Japan) was immersed in the Re solution for 4 hours at room temperature (25° C.). After immersion, water was distilled off in a rotary evaporator under reduced pressure, and drying was performed at 110° C.

After drying, in a Rh solution prepared by dissolving 0.0419 g of $RhCl_3$ in 50 mL of water, the zirconium oxide was immersed at room temperature (25° C.) for 4 hours. After immersion, water was distilled off using a rotary evaporator under reduced pressure, and drying was performed at 110° C. Then, the dried product was subjected to calcination in an air atmosphere in a muffle furnace at 500° C. for 3 hours, resulting in a catalyst (11) [Rh/Re/$ZrO_2$, amount of Rh supported: 0.2 mmol/g (support), amount of Re supported: 0.05 mmol/g (support), Re/Rh (molar ratio)=0.25].

Preparation Example 12

Preparation of Catalyst: Sequential Impregnation Method 0.0058 g of $NH_4VO_3$ was dissolved in 50 mL of water to prepare a V solution. 1.0 g of zirconium oxide ($ZrO_2$, specific surface area: 22.1 $m^2$/g, reference catalyst "JRC-ZRO-8" by the Catalysis Society of Japan) was immersed in the V solution for 4 hours at room temperature (25° C.). After immersion, water was distilled off in a rotary evaporator under reduced pressure, and drying was performed at 110° C.

After drying, in a Rh solution prepared by dissolving 0.0419 g of $RhCl_3$ in 50 mL of water, the zirconium oxide was immersed at room temperature (25° C.) for 4 hours. After immersion, water was distilled off using a rotary evaporator under reduced pressure, and drying was performed at 110° C. Then, the dried product was subjected to calcination in an air atmosphere in a muffle furnace at 500° C. for 3 hours, resulting in a catalyst (12) [Rh/V/$ZrO_2$, amount of Rh supported 0.2 mmol/g (support), amount of V supported: 0.05 mmol/g (support), V/Rh (molar ratio)=0.25].

Preparation Example 13

Preparation of Catalyst: Sequential Impregnation Method 0.0088 g of $(NH_4)_6Mo_7O_{24}\cdot 4H_2O$ was dissolved in 50 mL of water to prepare a Mo solution. 1.0 g of zirconium oxide ($ZrO_2$, specific surface area: 22.1 $m^2$/g, reference catalyst "JRC-ZRO-8" by the Catalysis Society of Japan) was immersed in the Mo solution for 4 hours at room temperature (25° C.). After immersion, water was distilled off in a rotary evaporator under reduced pressure, and drying was performed at 110° C.

After drying, in a Pd solution prepared by dissolving 0.0449 g of $Pd(OAc)_2$ in 50 mL of acetone, the zirconium oxide was immersed at room temperature (25° C.) for 4 hours. After immersion, water was distilled off using a rotary evaporator under reduced pressure, and drying was performed at 110° C. Then, the dried product was subjected to calcination in an air atmosphere in a muffle furnace at 500° C. for 3 hours, resulting in a catalyst (13) [Pd/Mo/$ZrO_2$, amount of Pd supported: 0.2 mmol/g (support), amount of Mo supported: 0.05 mmol/g (support), Mo/Pd (molar ratio)=0.25].

Preparation Example 14

Preparation of Catalyst: Sequential Impregnation Method 0.0128 g of $(NH_4)_{10}H_2(W_2O_7)_6$ was dissolved in 50 mL of water to prepare a W solution. 1.0 g of zirconium oxide ($ZrO_2$, specific surface area: 22.1 $m^2$/g, reference catalyst "JRC-ZRO-8" by the Catalysis Society of Japan) was immersed in the W solution for 4 hours at room temperature (25° C.). After immersion, water was distilled off in a rotary evaporator under reduced pressure, and drying was performed at 110° C.

After drying, in a Pd solution prepared by dissolving 0.0449 g of $Pd(OAc)_2$ in 50 mL of acetone, the zirconium oxide was immersed at room temperature (25° C.) for 4 hours. After immersion, water was distilled off using a rotary evaporator under reduced pressure, and drying was performed at 110° C. Then, the dried product was subjected to calcination in an air atmosphere in a muffle furnace at 500° C. for 3 hours, resulting in a catalyst (14) [Pd/W/$ZrO_2$, amount of Pd supported: 0.2 mmol/g (support), amount of W supported: 0.05 mmol/g (support), W/Pd (molar ratio)=0.25].

Preparation Example 15

Preparation of Catalyst: Sequential Impregnation Method 0.0088 g of $(NH_4)_6Mo_7O_{24}\cdot 4H_2O$ was dissolved in 50 mL of water to prepare a Mo solution. 1.0 g of zirconium oxide ($ZrO_2$, specific surface area: 22.1 $m^2$/g, reference catalyst "JRC-ZRO-8" by the Catalysis Society of Japan) was immersed in the Mo solution for 4 hours at room temperature (25° C.). After immersion, water was distilled off in a rotary evaporator under reduced pressure, and drying was performed at 110° C.

After drying, in a Ir solution prepared by dissolving 0.0814 g of $H_2IrCl_6$ in 50 mL of water, the zirconium oxide was immersed at room temperature (25° C.) for 4 hours. After immersion, water was distilled off using a rotary evaporator under reduced pressure, and drying was performed at 110° C. Then, the dried product was subjected to calcination in an air atmosphere in a muffle furnace at 500° C. for 3 hours, resulting in a catalyst (15) [Ir/Mo/$ZrO_2$, amount of Ir supported: 0.2 mmol/g (support), amount of Mo supported: 0.05 mmol/g (support), Mo/Ir (molar ratio)=0.25].

Preparation Example 16

Preparation of Catalyst: Sequential Impregnation Method 0.0134 g of $(NH_4)ReO_4$ was dissolved in 50 mL of water to prepare a Re solution. 1.0 g of zirconium oxide ($ZrO_2$, specific surface area: 22.1 $m^2$/g, reference catalyst "JRC-ZRO-8" by the Catalysis Society of Japan) was immersed in the Re solution for 4 hours at room temperature (25° C.). After immersion, water was distilled off in a rotary evaporator under reduced pressure, and drying was performed at 110° C.

After drying, in a Ir solution prepared by dissolving 0.0814 g of $H_2IrCl_6$ in 50 mL of water, the zirconium oxide was immersed at room temperature (25° C.) for 4 hours. After immersion, water was distilled off using a rotary evaporator under reduced pressure, and drying was performed at 110° C. Then, the dried product was subjected to calcination in an air atmosphere in a muffle furnace at 500° C. for 3 hours, resulting in a catalyst (16) [Ir/Re/$ZrO_2$, amount of Ir supported: 0.2 mmol/g (support), amount of Re supported: 0.05 mmol/g (support), Re/Ir (molar ratio)=0.25].

Preparation Example 17

Preparation of Catalyst: Sequential Impregnation Method 0.1530 g of $(NH_4)_{10}H_2(W_2O_7)_6$ was dissolved in 50 mL of water to prepare a W solution. 1.0 g of zirconium oxide ($ZrO_2$, specific surface area: 22.1 $m^2$/g, reference catalyst "JRC-ZRO-8" by the Catalysis Society of Japan) was immersed in the W solution for 4 hours at room temperature (25° C.). After immersion, water was distilled off in a rotary evaporator under reduced pressure, and drying was performed at 110° C.

After drying, in a Ir solution prepared by dissolving 0.0814 g of H2IrC16 in 50 mL of water, the zirconium oxide was immersed at room temperature (25° C.) for 4 hours. After immersion, water was distilled off using a rotary evaporator under reduced pressure, and drying was performed at 110° C. Then, the dried product was subjected to calcination in an air atmosphere in a muffle furnace at 500° C. for 3 hours, resulting in a catalyst (17) [Ir/W/$ZrO_2$, amount of Ir supported 0.2 mmol/g (support), amount of W supported: 0.05 mmol/g (support), W/Ir (molar ratio)=0.25].

Preparation Example 18

Preparation of Catalyst: Sequential Impregnation Method 0.0088 g of $(NH_4)_6Mo_7O_{24}\cdot 4H_2O$ was dissolved in 50 mL of water to prepare a Mo solution. 1.0 g of hydroxyapatite (HAP, trade name "Tricalcium Phosphate", available from FUJIFILM Wako Pure Chemical Corporation) was immersed in the Mo solution for 4 hours at room temperature (25° C.). After immersion, water was distilled off in a rotary evaporator under reduced pressure, and drying was performed at 110° C.

After drying, in a Pt solution prepared by dissolving 0.0820 g of $H_2PtCl_6$ in 50 mL of water, the hydroxyapatite was immersed at room temperature (25° C.) for 4 hours. After immersion, water was distilled off using a rotary evaporator under reduced pressure, and drying was performed at 110° C. Then, the dried product was subjected to calcination in an air atmosphere in a muffle furnace at 500° C. for 3 hours, resulting in a catalyst (18) [Pt/Mo/HAP, amount of Pt supported: 0.2 mmol/g (support), amount of Mo supported: 0.05 mmol/g (support), Mo/Pt (molar ratio)=0.25].

Preparation Example 19

Preparation of Catalyst: Sequential Impregnation Method 0.0066 g of $(NH_4)_6Mo_7O_{24}\cdot 4H_2O$ was dissolved in 50 mL of water to prepare a Mo solution. 1.5 g of zirconium oxide ($ZrO_2$, specific surface area: 22.1 $m^2$/g, a reference catalyst "JRC-ZRO-8" by the Catalysis Society of Japan) was immersed in the Mo solution for 12 hours at room temperature (25° C.). After immersion, water was distilled off using a rotary evaporator, and drying was performed at 110° C.

After drying, in a Pt solution prepared by dissolving 0.0820 g of $H_2PtCl_6$ in 50 mL of water, the zirconium oxide was immersed at room temperature (25° C.) for 12 hours. After immersion, water was distilled off using a rotary evaporator, and drying was performed at 110° C. Then, the dried product was subjected to calcination in an air atmosphere in a muffle furnace at 500° C. for 3 hours, resulting in a catalyst (19) [Pt/Mo/$ZrO_2$, amount of Pt supported: 0.13 mmol/g (support), amount of Mo supported: 0.025 mmol/g (support), Mo/Pt (molar ratio)=0.19].

Preparation Example 20

Preparation of Catalyst: Sequential Impregnation Method 0.0066 g of $(NH_4)_6Mo_7O_{24}\cdot 4H_2O$ was dissolved in 50 mL of water to prepare a Mo solution. 1.8 g of titanium oxide ($TiO_2$, specific surface area: 18.0 $m^2$/g, reference catalyst "JRC-TiO-2" by the Catalysis Society of Japan) was immersed in the Mo solution for 12 hours at room temperature (25° C.). After immersion, water was distilled off using a rotary evaporator, and drying was performed at 110° C.

After drying, in a Pt solution prepared by dissolving 0.0820 g of $H_2PtCl_6$ in 50 mL of water, the titanium oxide was immersed at room temperature (25° C.) for 12 hours. After immersion, water was distilled off using a rotary evaporator, and drying was performed at 110° C. Then, the dried product was subjected to calcination in an air atmosphere in a muffle furnace at 500° C. for 3 hours, resulting in a catalyst (20) [Pt/Mo/$TiO_2$, amount of Pt supported: 0.11 mmol/g (support), amount of Mo supported: 0.021 mmol/g (support), Mo/Pt (molar ratio)=0.19].

Preparation Example 21

Preparation of Catalyst: Sequential Impregnation Method 0.0066 g of $(NH_4)_6Mo_7O_{24}\cdot 4H_2O$ was dissolved in 50 mL of water to prepare a Mo solution. 0.56 g of hydroxyapatite (HAP, trade name "Tricalcium Phosphate", available from FUJIFILM Wako Pure Chemical Corporation) was immersed in the Mo solution for 12 hours at room temperature (25° C.). After immersion, water was distilled off in a rotary evaporator under reduced pressure, and drying was performed at 110° C.

After drying, in a Pt solution prepared by dissolving 0.0820 g of $H_2PtCl_6$ in 50 mL of water, the hydroxyapatite was immersed at room temperature (25° C.) for 12 hours. After immersion, water was distilled off using a rotary evaporator under reduced pressure, and drying was performed at 110° C. Then, the dried product was subjected to calcination in an air atmosphere in a muffle furnace at 500° C. for 3 hours, resulting in a catalyst (21) [Pt/Mo/HAP, amount of Pt supported: 0.36 mmol/g (support), amount of Mo supported: 0.067 mmol/g (support), Mo/Pt (molar ratio)=0.19].

Preparation Example 22

Preparation of Catalyst: Sequential Impregnation Method 0.0066 g of $(NH_4)_6Mo_7O_{24}\cdot 4H_2O$ was dissolved in 50 mL of water to prepare a Mo solution. 0.27 g of cerium oxide ($CeO_2$, specific surface area: 123.1 $m^2$/g, reference catalyst "JRC-CEO-2" by the Catalysis Society of Japan) was immersed in the Mo solution for 12 hours at room temperature (25° C.). After immersion, water was distilled off in a rotary evaporator under reduced pressure, and drying was performed at 110° C.

After drying, in a Pt solution prepared by dissolving 0.0820 g of $H_2PtCl_6$ in 50 mL of water, the cerium oxide was immersed at room temperature (25° C.) for 12 hours. After immersion, water was distilled off using a rotary evaporator under reduced pressure, and drying was performed at 110° C. Then, the dried product was subjected to calcination in an air atmosphere in a muffle furnace at 500° C. for 3 hours, resulting in a catalyst (22) [Pt/Mo/$CeO_2$, amount of Pt supported: 0.74 mmol/g (support), amount of Mo supported: 0.139 mmol/g (support), Mo/Pt (molar ratio)=0.19].

Example 1

1 mmol of methyl hexanoate serving as a substrate, 100 mg of catalyst (1) (Pt/Mo/$ZrO_2$) [Pt that is 2 mol % of the substrate, Mo that is 0.5 mol % of the substrate (in terms of metal)], and 3 mL of diisopropyl ether were placed in an autoclave having a Teflon (trade name) inner cylinder and reacted at 180° C. for 3 hours under 5 MPa of hydrogen pressure to form reaction products. A gas chromatograph-mass spectrometer (GC-MS) (internal standard method) was used to measure the conversion rate of the substrate (cony. [%]) and the yield of each reaction product (yield [%]). According to the result, the conversion rate of the substrate was 91%, and hexyl methyl ether, 1-hexanol, and hexane were produced (see the following Formula). The yield of hexyl methyl ether was 46%, the yield of 1-hexanol was 2%, and the yield of hexane was

[Chem. 4]

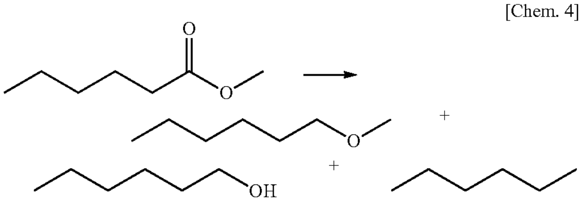

Example 2

The same procedure as in Example 1 was performed except that the catalyst (2) (Pt—Mo/$ZrO_2$) was used instead of the catalyst (1). According to the result, the conversion rate of the substrate was 89%, and hexyl methyl ether, 1-hexanol, and hexane were produced. The yield of hexyl methyl ether was 40%, the yield of 1-hexanol was 2%, and the yield of hexane was 25%.

Example 3

The same procedure as in Example 1 was performed except that the catalyst (3) (Mo/Pt/$ZrO_2$) was used instead of the catalyst (1). According to the result, the conversion rate of the substrate was 91%, and hexyl methyl ether, 1-hexanol, and hexane were produced. The yield of hexyl methyl ether was 42%, the yield of 1-hexanol was 3%, and the yield of hexane was 26%.

Example 4

The same procedure as in Example 1 was performed except that the reaction temperature was changed to 140° C. According to the result, the conversion rate of the substrate was 95%, and hexyl methyl ether, 1-hexanol, and hexane were produced. The yield of hexyl methyl ether was 59%, the yield of 1-hexanol was 1%, and the yield of hexane was 22%.

Comparative Example 1

The same procedure as in Example 1 was performed except that the catalyst (4) ($Mo/ZrO_2$) was used instead of the catalyst (1) and that the reaction temperature was changed to 140° C. According to the result, the conversion rate of the substrate was 1%. Hexyl methyl ether, 1-hexanol, and hexane were not produced.

Example 5

The same procedure as in Example 1 was performed except that the reaction time was changed to one hour. According to the result, the conversion rate of the substrate was 76%, and hexyl methyl ether, 1-hexanol, and hexane were produced. The yield of hexyl methyl ether was 42%, the yield of 1-hexanol was 2%, and the yield of hexane was 33%.

Example 6

The same procedure as in Example 1 was performed except that the reaction time was changed to 6 hours. According to the result, the conversion rate of the substrate was 97%, and hexyl methyl ether, 1-hexanol, and hexane were produced. The yield of hexyl methyl ether was 45%, the yield of 1-hexanol was 1%, and the yield of hexane was 14%.

Example 7

The same procedure as in Example 1 was performed except that the reaction time was changed to 12 hours. According to the result, the conversion rate of the substrate was 97%, and hexyl methyl ether, 1-hexanol, and hexane were produced. The yield of hexyl methyl ether was 46%, the yield of 1-hexanol was 2%, and the yield of hexane was 46%.

Example 8

The same procedure as in Example 1 was performed except that the reaction temperature was changed to 160° C. According to the result, the conversion rate of the substrate was 89%, and hexyl methyl ether, 1-hexanol, and hexane were produced. The yield of hexyl methyl ether was 49%, the yield of 1-hexanol was 2%, and the yield of hexane was 22%.

Example 9

The same procedure as in Example 1 was performed except that the reaction temperature was changed to 150° C. According to the result, the conversion rate of the substrate was 96%, and hexyl methyl ether, 1-hexanol, and hexane were produced. The yield of hexyl methyl ether was 48%, the yield of 1-hexanol was 1%, and the yield of hexane was 28%.

Example 10

The same procedure as in Example 1 was performed except that the reaction temperature was changed to 130° C. According to the result, the conversion rate of the substrate was 94%, and hexyl methyl ether, 1-hexanol, and hexane were produced. The yield of hexyl methyl ether was 50%, the yield of 1-hexanol was 2%, and the yield of hexane was 33%.

Example 11

The same procedure as in Example 1 was performed except that the reaction temperature was changed to 120° C. According to the result, the conversion rate of the substrate was 77%, and hexyl methyl ether, 1-hexanol, and hexane were produced. The yield of hexyl methyl ether was 49%, the yield of 1-hexanol was 7%, and the yield of hexane was 19%.

Example 12

The same procedure as in Example 1 was performed except that the reaction temperature was changed to 100° C. According to the result, the conversion rate of the substrate was 63%, and hexyl methyl ether, 1-hexanol, and hexane were produced. The yield of hexyl methyl ether was 35%, the yield of 1-hexanol was 12%, and the yield of hexane was 6%.

Example 13

The same procedure as in Example 1 was performed except that the reaction temperature was changed to 80° C. According to the result, the conversion rate of the substrate was 33%, and hexyl methyl ether, 1-hexanol, and hexane were produced. The yield of hexyl methyl ether was 16%, the yield of 1-hexanol was 10%, and the yield of hexane was 3%.

Example 14

The same procedure as in Example 1 was performed except that the solvent was changed to diethyl ether instead of diisopropyl ether and that the reaction time was changed to one hour. According to the result, the conversion rate of the substrate was 91%, and hexyl methyl ether and 1-hexanol were produced. Hexane was not produced. The yield of hexyl methyl ether was 53%, and the yield of 1-hexanol was 1%.

Example 15

The same procedure as in Example 1 was performed except that no solvent was used. According to the result, the conversion rate of the substrate was 99%, and hexyl methyl ether and hexane were produced. 1-Hexanol was not produced. The yield of hexyl methyl ether was 59%, and the yield of hexane was 39%.

Example 16

The same procedure as in Example 1 was performed except that the solvent was changed to octane instead of diisopropyl ether and that the reaction time was changed to 12 hours. According to the result, the conversion rate of the substrate was 82%, and hexyl methyl ether, 1-hexanol, and hexane were produced. The yield of hexyl methyl ether was 29%, the yield of 1-hexanol was 6%, and the yield of hexane was 38%.

Example 17

The same procedure as in Example 1 was performed except that the catalyst (5) (Pt/Re/$ZrO_2$) was used instead of the catalyst (1) and that the solvent was changed to diethyl ether instead of diisopropyl ether. According to the result, the conversion rate of the substrate was 56%, and hexyl methyl ether, 1-hexanol, and hexyl hexanoate were produced. The yield of hexyl methyl ether was 8%, the yield of 1-hexanol was 7%, and the yield of hexyl hexanoate was 1%.

Example 18

The same procedure as in Example 1 was performed except that the catalyst (6) (Pt/W/$ZrO_2$) was used instead of the catalyst (1) and that the solvent was changed to diethyl ether instead of diisopropyl ether. According to the result, the conversion rate of the substrate was 42%, and hexyl methyl ether was produced. The yield of hexyl methyl ether was 6%.

Example 19

The same procedure as in Example 1 was performed except that the catalyst (7) (Pt/V/$ZrO_2$) was used instead of the catalyst (1) and that the solvent was changed to diethyl ether instead of diisopropyl ether. According to the result, the conversion rate of the substrate was 32%, and hexyl methyl ether and 1-hexanol were produced. The yield of hexyl methyl ether was 1%, and the yield of 1-hexanol was 5%.

Example 20

The same procedure as in Example 1 was performed except that the catalyst (8) (Ru/Re/$ZrO_2$) was used instead of the catalyst (1) and that the solvent was changed to diethyl ether instead of diisopropyl ether. According to the result, the conversion rate of the substrate was 44%, and hexyl methyl ether, 1-hexanol, and hexyl hexanoate were produced. The yield of hexyl methyl ether was 4%, the yield of 1-hexanol was 4%, and the yield of hexyl hexanoate was 1%.

Example 21

The same procedure as in Example 1 was performed except that the catalyst (9) (Ru/W/$ZrO_2$) was used instead of the catalyst (1) and that the solvent was changed to diethyl ether instead of diisopropyl ether. According to the result, the conversion rate of the substrate was 30%, and hexyl methyl ether was produced. The yield of hexyl methyl ether was 5%.

Example 22

The same procedure as in Example 1 was performed except that the catalyst (10) (Ru/V/$ZrO_2$) was used instead of the catalyst (1) and that the solvent was changed to diethyl ether instead of diisopropyl ether. According to the result, the conversion rate of the substrate was 32%, and hexyl methyl ether and 1-hexanol were produced. The yield of hexyl methyl ether was 1%, and the yield of 1-hexanol was 5%.

Example 23

The same procedure as in Example 1 was performed except that the catalyst (11) (Rh/Re/$ZrO_2$) was used instead of the catalyst (1) and that the solvent was changed to diethyl ether instead of diisopropyl ether. According to the result, the conversion rate of the substrate was 42%, and hexyl methyl ether, 1-hexanol, and hexyl hexanoate were produced. The yield of hexyl methyl ether was 1%, the yield of 1-hexanol was 3%, and the yield of hexyl hexanoate was 1%.

Example 24

The same procedure as in Example 1 was performed except that the catalyst (12) (Rh/V/$ZrO_2$) was used instead of the catalyst (1) and that the solvent was changed to diethyl ether instead of diisopropyl ether. According to the result, the conversion rate of the substrate was 23%, and hexyl methyl ether was produced. The yield of hexyl methyl ether was 1%.

Example 25

The same procedure as in Example 1 was performed except that the catalyst (13) (Pd/Mo/$ZrO_2$) was used instead of the catalyst (1) and that the solvent was changed to diethyl ether instead of diisopropyl ether. According to the result, the conversion rate of the substrate was 35%, and hexyl methyl ether and 1-hexanol were produced. The yield of hexyl methyl ether was 3%, and the yield of 1-hexanol was %.

Example 26

The same procedure as in Example 1 was performed except that the catalyst (14) (Pd/W/$ZrO_2$) was used instead of the catalyst (1) and that the solvent was changed to diethyl ether instead of diisopropyl ether. According to the result, the conversion rate of the substrate was 30%, and hexyl methyl ether was produced. The yield of hexyl methyl ether was 2%.

Example 27

The same procedure as in Example 1 was performed except that the catalyst (15) (Ir/Mo/$ZrO_2$) was used instead of the catalyst (1) and that the solvent was changed to diethyl ether instead of diisopropyl ether. According to the result, the conversion rate of the substrate was 43%, and hexyl methyl ether, 1-hexanol, and hexyl hexanoate were produced. The yield of hexyl methyl ether was 3%, the yield of 1-hexanol was 4%, and the yield of hexyl hexanoate was 1%.

Example 28

The same procedure as in Example 1 was performed except that the catalyst (16) (Ir/Re/$ZrO_2$) was used instead of the catalyst (1) and that the solvent was changed to diethyl ether instead of diisopropyl ether. According to the result, the conversion rate of the substrate was 32%, and hexyl methyl ether, 1-hexanol, and hexyl hexanoate were produced. The yield of hexyl methyl ether was 1%, the yield of 1-hexanol was 5%, and the yield of hexyl hexanoate was 1%.

Example 29

The same procedure as in Example 1 was performed except that the catalyst (17) (Ir/W/$ZrO_2$) was used instead of the catalyst (1) and that the solvent was changed to diethyl ether instead of diisopropyl ether. According to the result, the conversion rate of the substrate was 40%, and hexyl methyl ether was produced. The yield of hexyl methyl ether was 3%.

Example 30

The same procedure as in Example 1 was performed except that the catalyst (18) (Pt/Mo/HAP) was used instead of the catalyst (1) and that the solvent was changed to diethyl ether instead of diisopropyl ether. According to the result, the conversion rate of the substrate was 73%, and hexyl methyl ether and 1-hexanol were produced. The yield of hexyl methyl ether was 16%, and the yield of 1-hexanol was 6%.

Example 31

1 mmol (0.142 g) of cyclohexyl acetate serving as a substrate, 0.15 g of catalyst (19) (Pt/Mo/$ZrO_2$) [Pt that is 2 mol % of the substrate, Mo that is 0.375 mol % of the substrate (in terms of metal)], and 3 mL of n-hexane were placed in an autoclave having a Teflon (trade name) inner cylinder and reacted at 100° C. for 4 hours under 5 atm of hydrogen pressure to form reaction products. A gas chromatograph-mass spectrometer (GC-MS) (internal standard method) was used to measure the conversion rate of the substrate (cony. [%]) and the yield of each reaction product (yield [%]). According to the result, the conversion rate of the substrate was 97%, and cyclohexyl ethyl ether and cyclohexane were produced (see the following Formula). The yield of cyclohexyl ethyl ether was 70%, and the yield of cyclohexane was 23%. Note that cyclohexyl alcohol was not produced.

[Chem. 5]

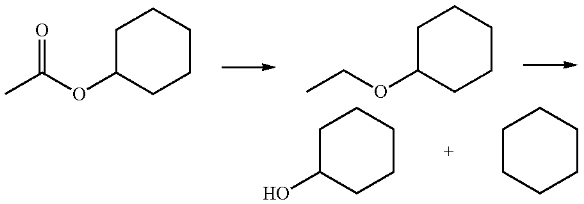

Example 32

0.25 mmol (0.036 g) of cyclohexyl acetate serving as a substrate, 0.0375 g of catalyst (19) (Pt/Mo/$ZrO_2$) [Pt that is 2 mol % of the substrate, Mo that is 0.375 mol % of the substrate (in terms of metal)], and 0.8 mL of n-hexane were placed in an autoclave having a Teflon (trade name) inner cylinder and reacted at 100° C. for 8 hours under 1 atm of hydrogen pressure to form reaction products. A gas chromatograph-mass spectrometer (GC-MS) (internal standard method) was used to measure the conversion rate of the substrate (cony. [%]) and the yield of each reaction product (yield [%]). According to the result, the conversion rate of the substrate was 100%, and cyclohexyl ethyl ether and cyclohexane were produced. The yield of cyclohexyl ethyl ether was 57%, and the yield of cyclohexane was 26%. Note that cyclohexyl alcohol was not produced.

Example 33

The catalyst used in Example 31 was recovered by centrifugation, dried in air at 110° C. for 3 hours, and treated under oxygen gas flow at 300° C. for 20 minutes. The recovered catalyst was used to perform an experiment under the same conditions as in Example 31. According to the result, the conversion rate of the substrate was 97%, and cyclohexyl ethyl ether and cyclohexane were produced. The yield of cyclohexyl ethyl ether was 67%, and the yield of cyclohexane was 25%. Note that cyclohexyl alcohol was not produced.

Example 34

21.1 mmol (3 g) of cyclohexyl acetate serving as a substrate, 0.45 g of catalyst (19) (Pt/Mo/$ZrO_2$), and 30 mL of n-hexane were placed in an autoclave having a Teflon (trade name) inner cylinder and reacted at 100° C. for 112 hours under 50 atm of hydrogen pressure to form reaction products. A gas chromatograph-mass spectrometer (GC-MS) (internal standard method) was used to measure the conversion rate of the substrate (cony. [%]) and the yield of each reaction product (yield [%]). According to the result, the conversion rate of the substrate was 88%, and cyclohexyl ethyl ether, cyclohexyl alcohol, and cyclohexane were produced. The yield of cyclohexyl ethyl ether was 58%, the yield of cyclohexyl alcohol was 6%, and the yield of cyclohexane was 21%.

Example 35

1 mmol (0.142 g) of cyclohexyl acetate serving as a substrate, 0.180 g of catalyst (20) (Pt/Mo/$TiO_2$) [Pt that is 2 mol % of the substrate, Mo that is 0.375 mol % of the substrate (in terms of metal)], and 3 mL of n-hexane were placed in an autoclave having a Teflon (trade name) inner cylinder and reacted at 100° C. for 4 hours under 5 atm of hydrogen pressure to form reaction products. A gas chromatograph-mass spectrometer (GC-MS) (internal standard method) was used to measure the conversion rate of the substrate (cony. [%]) and the yield of each reaction product (yield [%]). According to the result, the conversion rate of the substrate was 87%, and cyclohexyl ethyl ether and cyclohexane were produced. The yield of cyclohexyl ethyl ether was 52%, and the yield of cyclohexane was 28%. Note that although cyclohexyl alcohol was produced, the yield was less than 1%.

Example 36

1 mmol (0.142 g) of cyclohexyl acetate serving as a substrate, 0.060 g of catalyst (21) (Pt/Mo/HAP) [Pt that is 2 mol % of the substrate, Mo that is 0.375 mol % of the substrate (in terms of metal)], and 3 mL of n-hexane were placed in an autoclave having a Teflon (trade name) inner cylinder and reacted at 100° C. for 4 hours under 5 atm of hydrogen pressure to form reaction products. A gas chromatograph-mass spectrometer (GC-MS) (internal standard method) was used to measure the conversion rate of the substrate (cony. [%]) and the yield of each reaction product (yield [%]). According to the result, the conversion rate of the substrate was 30%, and cyclohexyl ethyl ether, cyclohexyl alcohol, and cyclohexane were produced. The yield of cyclohexyl ethyl ether was 19%, the yield of cyclohexyl alcohol was 1%, and the yield of cyclohexane was 10%.

Example 37

1 mmol (0.142 g) of cyclohexyl acetate serving as a substrate, 0.031 g of catalyst (22) ($Pt/Mo/CeO_2$) [Pt that is 2 mol % of the substrate, Mo that is 0.375 mol % of the substrate (in terms of metal)], and 3 mL of n-hexane were placed in an autoclave having a Teflon (trade name) inner cylinder and reacted at 100° C. for 4 hours under 5 atm of hydrogen pressure to form reaction products. A gas chromatograph-mass spectrometer (GC-MS) (internal standard method) was used to measure the conversion rate of the substrate (cony. [%]) and the yield of each reaction product (yield [%]). According to the result, the conversion rate of the substrate was 4%, and cyclohexyl ethyl ether, cyclohexyl alcohol, and cyclohexane were produced. The yield of cyclohexyl ethyl ether was 1%, the yield of cyclohexyl alcohol was 2%, and the yield of cyclohexane was 1%.

Example 38

1 mmol (0.142 g) of cyclohexyl acetate serving as a substrate, 0.15 g of catalyst (19) ($Pt/Mo/ZrO_2$) [Pt that is 2 mol % of the substrate, Mo that is 0.375 mol % of the substrate (in terms of metal)], and 3 mL of ethanol were placed in an autoclave having a Teflon (trade name) inner cylinder and reacted at 100° C. for 4 hours under 5 atm of hydrogen pressure to form reaction products. A gas chromatograph-mass spectrometer (GC-MS) (internal standard method) was used to measure the conversion rate of the substrate (cony. [%]) and the yield of each reaction product (yield [%]). According to the result, the conversion rate of the substrate was 22%, and cyclohexyl ethyl ether and cyclohexyl alcohol were produced. The yield of cyclohexyl ethyl ether was 12%, and the yield of cyclohexyl alcohol was 7%. Cyclohexane was not produced.

Example 39

1 mmol (0.142 g) of cyclohexyl acetate serving as a substrate, 0.15 g of catalyst (19) ($Pt/Mo/ZrO_2$) [Pt that is 2 mol % of the substrate, Mo that is 0.375 mol % of the substrate (in terms of metal)], and 3 mL of diisopropyl ether were placed in an autoclave having a Teflon (trade name) inner cylinder and reacted at 90° C. for 5 hours under 5 atm of hydrogen pressure to form reaction products. A gas chromatograph-mass spectrometer (GC-MS) (internal standard method) was used to measure the conversion rate of the substrate (cony. [%]) and the yield of each reaction product (yield [%]). The selectivity (%) of cyclohexyl ethyl ether was calculated (selectivity [%]=number of moles of cyclohexyl ethyl ether produced/number of moles of cyclohexyl acetate converted×100). According to the result, the conversion rate of the substrate was 63%, and cyclohexyl ethyl ether, cyclohexyl alcohol, and cyclohexane were produced. The yield of cyclohexyl ethyl ether was 48% (selectivity of 76%), the yield of cyclohexyl alcohol was 5%, and the yield of cyclohexane was 10%.

Example 40

The same procedure as in Example 39 was performed except that the reaction temperature was changed to 100° C. and that the reaction time was changed to 4 hours. According to the result, the conversion rate of the substrate was 89%, and cyclohexyl ethyl ether, cyclohexyl alcohol, and cyclohexane were produced. The yield of cyclohexyl ethyl ether was 68% (selectivity of 76%), the yield of cyclohexyl alcohol was 1%, and the yield of cyclohexane was 18%.

Example 41

The same procedure as in Example 39 was performed except that the reaction temperature was changed to 100° C. According to the result, the conversion rate of the substrate was 77%, and cyclohexyl ethyl ether, cyclohexyl alcohol, and cyclohexane were produced. The yield of cyclohexyl ethyl ether was 60% (selectivity of 78%), the yield of cyclohexyl alcohol was 2%, and the yield of cyclohexane was 18%.

Example 42

The same procedure as in Example 39 was performed except that the reaction temperature was changed to 120° C. and that the reaction time was changed to 4 hours.

According to the result, the conversion rate of the substrate was 99%, and cyclohexyl ethyl ether and cyclohexane were produced. The yield of cyclohexyl ethyl ether was 66% (selectivity of 67%), and the yield of cyclohexane was 29%. Note that cyclohexyl alcohol was not produced.

Example 43

The same procedure as in Example 39 was performed except that the reaction temperature was changed to 100° C., that the hydrogen pressure was changed to 10 atm, and that the reaction time was changed to 4 hours. According to the result, the conversion rate of the substrate was 95%, and cyclohexyl ethyl ether, cyclohexyl alcohol, and cyclohexane were produced. The yield of cyclohexyl ethyl ether was 72% (selectivity of 76%), the yield of cyclohexyl alcohol was 2%, and the yield of cyclohexane was 19%.

Example 44

1 mmol (0.142 g) of cyclohexyl acetate serving as a substrate, 0.15 g of catalyst (19) ($Pt/Mo/ZrO_2$) [Pt that is 2 mol % of the substrate, Mo that is 0.375 mol % of the substrate (in terms of metal)], and 3 mL of diisopropyl ether were placed in an autoclave having a Teflon (trade name) inner cylinder and reacted at 100° C. for 4 hours under 2 atm of hydrogen pressure to form reaction products. A gas chromatograph-mass spectrometer (GC-MS) (internal standard method) was used to measure the conversion rate of the substrate (cony. [%]) and the yield of each reaction product (yield [%]). The selectivity (%) of cyclohexyl ethyl ether was calculated (selectivity [%]=number of moles of cyclohexyl ethyl ether produced/number of moles of cyclohexyl acetate converted×100). According to the result, the conversion rate of the substrate was 87%, and cyclohexyl ethyl ether, cyclohexyl alcohol, and cyclohexane were produced. The yield of cyclohexyl ethyl ether was 62% (selectivity of 71%), the yield of cyclohexyl alcohol was approximately a trace amount, and the yield of cyclohexane was 22%.

Example 45

The same procedure as in Example 44 was performed except that the hydrogen pressure was changed to 3 atm. According to the result, the conversion rate of the substrate was 94%, and cyclohexyl ethyl ether, cyclohexyl alcohol, and cyclohexane were produced. The yield of cyclohexyl ethyl ether was 66% (selectivity of 70%), the yield of cyclohexyl alcohol was approximately a trace amount, and the yield of cyclohexane was 18%.

Example 46

The same procedure as in Example 44 was performed except that the hydrogen pressure was changed to 3.5 atm. According to the result, the conversion rate of the substrate was 90%, and cyclohexyl ethyl ether, cyclohexyl alcohol, and cyclohexane were produced. The yield of cyclohexyl ethyl ether was 71% (selectivity of 79%), the yield of cyclohexyl alcohol was 1%, and the yield of cyclohexane was 20%.

Example 47

The same procedure as in Example 44 was performed except that the hydrogen pressure was changed to 8 atm. According to the result, the conversion rate of the substrate was 91%, and cyclohexyl ethyl ether, cyclohexyl alcohol, and cyclohexane were produced. The yield of cyclohexyl ethyl ether was 72% (selectivity of 79%), the yield of cyclohexyl alcohol was 2%, and the yield of cyclohexane was 17%.

Example 48

1 mmol (0.142 g) of cyclohexyl acetate serving as a substrate, 0.15 g of catalyst (19) ($Pt/Mo/ZrO_2$) [Pt that is 2 mol % of the substrate, Mo that is 0.375 mol % of the substrate (in terms of metal)], and 3 mL of diisopropyl ether were placed in an autoclave having a Teflon (trade name) inner cylinder and reacted at 100° C. for 2 hours under 3 atm of hydrogen pressure to form reaction products. A gas chromatograph-mass spectrometer (GC-MS) (internal standard method) was used to measure the conversion rate of the substrate (cony. [%]) and the yield of each reaction product (yield [%]). The selectivity (%) of cyclohexyl ethyl ether was calculated (selectivity [%]=number of moles of cyclohexyl ethyl ether produced/number of moles of cyclohexyl acetate converted×100). According to the result, the conversion rate of the substrate was 20%, and cyclohexyl ethyl ether and cyclohexyl alcohol were produced. The yield of cyclohexyl ethyl ether was 17% (selectivity of 72%), and the yield of cyclohexyl alcohol was 5%. Cyclohexane was not produced.

Example 49

The same procedure as in Example 48 was performed except that the reaction temperature was changed to 120° C. According to the result, the conversion rate of the substrate was 50%, and cyclohexyl ethyl ether, cyclohexyl alcohol, and cyclohexane were produced. The yield of cyclohexyl ethyl ether was 34% (selectivity of 69%), the yield of cyclohexyl alcohol was 2%, and the yield of cyclohexane was 12%.

Example 50

The same procedure as in Example 48 was performed except that the reaction temperature was changed to 120° C. and that the reaction time was changed to 4 hours. According to the result, the conversion rate of the substrate exceeded 99%, and cyclohexyl ethyl ether and cyclohexane were produced. The yield of cyclohexyl ethyl ether was 66% (selectivity of 66%), and the yield of cyclohexane was 33%. Note that cyclohexyl alcohol was not produced.

Example 51

The same procedure as in Example 48 was performed except that the reaction temperature was changed to 140° C. According to the result, the conversion rate of the substrate was 45%, and cyclohexyl ethyl ether, cyclohexyl alcohol, and cyclohexane were produced. The yield of cyclohexyl ethyl ether was 25% (selectivity of 57%), the yield of cyclohexyl alcohol was approximately a trace amount, and the yield of cyclohexane was 13%.

Example 52

The same procedure as in Example 48 was performed except that the reaction temperature was changed to 140° C. and that the reaction time was changed to 4 hours. According to the result, the conversion rate of the substrate was 100%, and cyclohexyl ethyl ether and cyclohexane were produced. The yield of cyclohexyl ethyl ether was 57% (selectivity of 57%), and the yield of cyclohexane was 31%. Note that cyclohexyl alcohol was not produced.

Example 53

0.5 mmol (0.071 g) of cyclohexyl acetate serving as a substrate, 0.075 g of catalyst (19) ($Pt/Mo/ZrO_2$) [Pt that is 2 mol % of the substrate, Mo that is 0.375 mol % of the substrate (in terms of metal)], and 3 mL of n-hexane were placed in an autoclave (internal volume of 100 mL) having a Teflon (trade name) inner cylinder and reacted at 100° C. for 8 hours under 1 atm of hydrogen pressure to form reaction products. A gas chromatograph-mass spectrometer (GC-MS) (internal standard method) was used to measure the conversion rate of the substrate (cony. [%]) and the yield of each reaction product (yield [%]). According to the result, the conversion rate of the substrate was 99%, and cyclohexyl ethyl ether and cyclohexane were produced. The yield of cyclohexyl ethyl ether was 61%, and the yield of cyclohexane was 35%. Note that cyclohexyl alcohol was not produced.

Example 54

1 mmol (0.142 g) of cyclohexyl acetate serving as a substrate, 0.15 g of catalyst (19) ($Pt/Mo/ZrO_2$) [Pt that is 2 mol % of the substrate, Mo that is 0.375 mol % of the substrate (in terms of metal)], and 3 mL of n-hexane were placed in an autoclave (internal volume of 100 mL) having a Teflon (trade name) inner cylinder and reacted at 25° C. for 168 hours under 50 atm of hydrogen pressure to form reaction products. A gas chromatograph-mass spectrometer (GC-MS) (internal standard method) was used to measure the conversion rate of the substrate (cony. [%]) and the yield of each reaction product (yield [%]). According to the result, the conversion rate of the substrate was 10%, and cyclohexyl ethyl ether and cyclohexyl alcohol were produced. The yield of cyclohexyl ethyl ether was 2%, and the yield of cyclohexyl alcohol was 5%. Cyclohexane was not produced.

As a summary of the above, configurations and variations of the present disclosure are described below.

[1] A method for producing an ether, the method including reducing a carboxylic acid ester with molecular hydrogen in the presence of the following Catalyst and producing a corresponding ether in which a —C(═O)O— group of the carboxylic acid ester has been converted to a —$CH_2O$— group.

Catalyst: a catalyst in which the following $M^1$ and $M^2$ are supported as metal species on the following Support:

$M^1$: platinum, ruthenium, rhodium, palladium, or iridium $M^2$: molybdenum, rhenium, tungsten, or vanadium Support: zirconium oxide, titanium oxide, cerium oxide, or hydroxyapatite

[2] The method for producing an ether according to [1], wherein the carboxylic acid ester is a compound represented by Formula (1) above, where $R^1$ is a hydrogen atom, or an organic group having a carbon atom at an adjacent site to the carbonyl group in the Formula, and $R^2$ is an organic group having a carbon atom at a binding site with an oxygen atom in the Formula.

[3] The method for producing an ether according to [1] or [2], wherein the Catalyst contains $M^2$ as a metal species in a range of from 0.05 to 1 mol per 1 mol of $M^1$ that is a metal species.

[4] The method for producing an ether according to any one of [1] to [3], wherein an amount of $M^1$ supported (in terms of metal) in the catalyst is from 0.01 to 10 mmol/g with respect to the support.

[5] The method for producing an ether according to any one of [1] to [4], wherein an amount of $M^2$ supported (in terms of metal) in the catalyst is from 0.001 to 1 mmol/g with respect to the support.

[6] The method for producing an ether according to any one of [1] to [5], wherein a specific surface area of the support is from 5 to 250 $m^2/g$.

[7] The method for producing an ether according to any one of [1] to [6], wherein a reaction temperature of the reduction reaction is from 20 to 250° C.

[8] The method of producing an ether according to any one of [1] to [7], wherein a hydrogen pressure during the reduction reaction is from 0.1 to 20 MPa.

[9] An ester reduction catalyst in which the following $M^1$ and $M^2$ are supported as metal species on the following Support, the catalyst for use in reducing a carboxylic acid ester to give a corresponding ether in which a —C(═O)O— group of the carboxylic acid ester has been converted to a —$CH_2O$— group:

$M^1$: platinum, ruthenium, rhodium, palladium, or iridium $M^2$: molybdenum, rhenium, tungsten, or vanadium Support: zirconium oxide, titanium oxide, cerium oxide, or hydroxyapatite The ester reduction catalyst according to [9], wherein the catalyst contains $M^2$ as a metal species in a range of from 0.05 to 1 mol per 1 mol of $M^1$ that is a metal species.

The ester reduction catalyst according to [9] or [10], wherein an amount of $M^1$ supported (in terms of metal) is from 0.01 to 10 mmol/g with respect to the support.

The ester reduction catalyst according to any one of [9] to [11], wherein an amount of $M^2$ supported (in terms of metal) is from 0.001 to 1 mmol/g with respect to the support.

[13] The ester reduction catalyst according to any one of [9] to [12], wherein a specific surface area of the support is from 5 to 250 $m^2/g$.

INDUSTRIAL APPLICABILITY

According to the method for producing an ether and the ester reduction catalyst of an embodiment of the present disclosure, a corresponding ether can be produced by reducing a carboxylic acid ester with molecular hydrogen without a large amount of salt waste or hazardous waste being discharged. Furthermore, separation of reaction products and catalyst is easy since the catalyst is a heterogeneous catalyst. The present disclosure allows for not only a reaction in a solvent but also a reaction without a solvent. The present disclosure enables the synthesis of not only symmetrical ethers but also asymmetrical ethers, giving it a wide range of application.

The invention claimed is:

1. A method for producing an ether, the method comprising reducing a carboxylic acid ester with molecular hydrogen in the presence of the following Catalyst and producing a corresponding ether in which a —C(═O)O— group of the carboxylic acid ester has been converted to a —$CH_2O$— group:

Catalyst: a catalyst in which the following $M^1$ and M2 are supported as metal species on the following Support:

$M^1$: platinum $M^2$: molybdenum, rhenium, tungsten, or vanadium

Support: zirconium oxide, titanium oxide, cerium oxide, or hydroxyapatite.

2. The method for producing an ether according to claim 1, wherein the carboxylic acid ester is a compound represented by Formula (1):

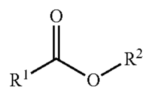

(1)

where in Formula (1), $R^1$ is a hydrogen atom or an organic group having a carbon atom at an adjacent site to the carbonyl group in the Formula, and $R^2$ is an organic group having a carbon atom at a binding site to an oxygen atom in the Formula.

3. The method for producing an ether according to claim 1, wherein the catalyst contains $M^2$ as a metal species in a range of from 0.05 to 1 mol per 1 mol of $M^1$ that is a metal species.

4. The method for producing an ether according to claim 1, wherein a reaction temperature of the reduction reaction is from 20 to 250° C.

5. The method of producing an ether according to claim 1, wherein a hydrogen pressure during the reduction reaction is from 0.1 to 20 MPa.

6. The method of producing an ether according to claim 1, wherein the metal species $M^2$ is molybdenum.

* * * * *